US006999807B2

(12) United States Patent
Smith et al.

(10) Patent No.: US 6,999,807 B2
(45) Date of Patent: Feb. 14, 2006

(54) PH MEASURING BALLOON

(75) Inventors: Scott R. Smith, Chaska, MN (US); Jaydeep Y. Kokate, Maple Grove, MN (US); Leonard B. Richardson, Minneapolis, MN (US); Eric M. Dobrava, Champlin, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/349,674

(22) Filed: Jan. 23, 2003

(65) Prior Publication Data
US 2004/0147845 A1    Jul. 29, 2004

(51) Int. Cl.
  A61B 5/00    (2006.01)
(52) U.S. Cl. .................... 600/310; 600/317; 600/342
(58) Field of Classification Search ........ 600/309–310, 600/342, 317, 322, 341
See application file for complete search history.

(56) References Cited

U.S. PATENT DOCUMENTS

| | | | |
|---|---|---|---|
| 4,476,870 A | 10/1984 | Peterson et al. | |
| 4,579,641 A * | 4/1986 | Shimomura et al. | 600/361 |
| 4,592,361 A | 6/1986 | Parker et al. | |
| 4,606,351 A | 8/1986 | Lübbers | |
| 4,652,143 A | 3/1987 | Wickersheim et al. | |
| 4,803,049 A * | 2/1989 | Hirschfeld et al. | 422/58 |
| 4,810,655 A | 3/1989 | Khalil et al. | |
| 4,895,156 A | 1/1990 | Schulze | |
| 4,928,694 A | 5/1990 | Maxwell | |
| 4,934,369 A | 6/1990 | Maxwell | |
| 5,012,809 A | 5/1991 | Shulze | |
| 5,046,501 A | 9/1991 | Crilly | |
| 5,047,627 A | 9/1991 | Yim et al. | |
| 5,048,525 A | 9/1991 | Maxwell | |
| 5,127,405 A | 7/1992 | Alcala et al. | |
| 5,197,470 A * | 3/1993 | Helfer et al. | 600/473 |
| 5,217,456 A | 6/1993 | Narciso, Jr. | |
| 5,304,495 A | 4/1994 | Yim | 436/68 |
| 5,335,658 A | 8/1994 | Bedingham | |
| 5,348,003 A * | 9/1994 | Caro | 600/310 |
| 5,421,328 A | 6/1995 | Bedingham | |
| 5,433,216 A * | 7/1995 | Sugrue et al. | 600/591 |
| 5,439,476 A * | 8/1995 | Frantzides | 600/207 |
| 5,607,644 A | 3/1997 | Olstein et al. | 422/82.07 |
| 5,626,134 A | 5/1997 | Zuckerman | |
| 5,641,633 A | 6/1997 | Linn et al. | |
| 5,648,270 A | 7/1997 | Kuhn et al. | |
| 5,708,957 A | 1/1998 | Chuang et al. | |
| 5,788,631 A | 8/1998 | Fiddian-Green | 600/309 |

(Continued)

FOREIGN PATENT DOCUMENTS

DE    3523987 A  *  1/1987

(Continued)

Primary Examiner—Eric F. Winakur
(74) Attorney, Agent, or Firm—Fish & Richardson P.C., P.A.

(57) ABSTRACT

The present invention relates to devices and methods for measuring the pH of blood in the vicinity of a vulnerable plaque. A balloon including an opto-electric device may be positioned proximate a vulnerable plaque. The balloon can be inflated to partially occlude blood flow enabling interaction between lipid laden blood and pH-sensitive material either within the balloon or on the wall(s) of the balloon. The selected pH-sensitive material is one whose optical properties change as a function of the pH of blood in the vasculature. An opto-electric device may be used for measuring the optical property and/or the change in the optical characteristics of the pH-sensitive compound.

49 Claims, 1 Drawing Sheet

U.S. PATENT DOCUMENTS

| | | |
|---|---|---|
| 5,804,395 A | 9/1998 | Schade et al. |
| 5,830,138 A | 11/1998 | Wilson |
| 5,882,936 A | 3/1999 | Bentsen et al. ............... 436/68 |
| 6,004,315 A * | 12/1999 | Dumont ....................... 606/15 |
| 6,107,083 A | 8/2000 | Collins et al. |
| 6,254,831 B1 | 7/2001 | Barnard et al. |
| 6,325,978 B1 | 12/2001 | Labuda et al. |
| 6,498,941 B1 | 12/2002 | Jackson ..................... 600/310 |
| 2002/0026108 A1 | 2/2002 | Colvin, Jr. .................. 600/316 |
| 2005/0049475 A1 * | 3/2005 | Gregersen ................... 600/407 |

FOREIGN PATENT DOCUMENTS

| | | |
|---|---|---|
| GB | 2 132 348 A | 7/1984 |
| WO | WO 92/19957 | 11/1992 |
| WO | WO02/47751 | 6/2002 |

* cited by examiner

PH MEASURING BALLOON

FIELD OF THE INVENTION

The present invention relates generally to methods and devices for detecting vulnerable plaque within a blood vessel. More specifically, the present invention relates to methods and devices for measuring the pH of blood in the vicinity of a vulnerable plaque.

BACKGROUND OF THE INVENTION

It is widely recognized that plaques or lesions within body vasculature may be classified into three broad categories, viz., calcified or hard, fibrous, or inflamed lipid filled plaque. The detection and identification of inflamed plaques is important since such lesions are at the greatest risk of rupture, resulting in a large thrombus or blood clot to form and occlude the flow of blood through the artery, thereby causing irreversible injury to the heart or brain.

An inflamed or vulnerable plaque may be characterized by its cap thickness, lipid pool size, and the pondus Hydrogenii (pH) of the blood in its vicinity. In general, the pH of the blood in the vicinity, or at an immediately distal location, of such lesions may be somewhat lower than normal. Additionally, the region of an inflamed plaque is relatively warmer than the surrounding tissue. Numerous devices such as fiber optic systems with infra-red detectors have been proposed, however, such devices are very expensive, making them available only in a limited number of procedures. Therefore, there is a need for a relatively inexpensive means of detecting vulnerable plaque within the blood vessel.

SUMMARY OF THE INVENTION

The present invention pertains to a balloon catheter which may be inserted into a body lumen and advanced to the suspected location of a vulnerable plaque for determining the pH of the blood in the vicinity of the lesion.

In one illustrative embodiment of the present invention, the balloon may be a double-walled balloon disposed about a portion of a catheter proximate the distal end of the catheter. The double-walled balloon may have a first material forming an outer wall and a second material forming an inner wall, with a space between the inner and outer walls. The outer wall of the balloon may be of a material permeable to lipid laden blood, thereby permitting blood to enter the space enclosed between the inner and outer walls.

In one embodiment of the invention, the space between the inner and outer walls of the double-walled balloon may be filled with a pH-sensitive material such that the optical property thereof changes in response to the pH of the blood.

Another embodiment of the invention may have a single-walled balloon disposed about a portion of the catheter proximate the distal end of the catheter. In such an embodiment, the balloon wall may be of a material permeable to lipid laden blood, thereby permitting blood to enter the space enclosed by the single-walled balloon.

In other embodiments, the one or more balloon walls may be coated, at least in part, by a pH-sensitive material whose optical properties may change in response to the pH of the blood. In yet other embodiments, the balloon wall(s) itself may be of a material whose optical properties may change in response to the pH of the blood.

The balloon wall(s) may, at least in part, be transparent to at least one predetermined wavelength of light. Additionally, the optical properties of the balloon wall(s) and/or the pH-sensitive compound enclosed between the inner and outer walls of a double-walled balloon may change in response to the pH.

Changes in the optical properties of the balloon wall(s) and/or the pH-sensitive compound may be determined by an opto-electric device mounted on the catheter and enclosed by the balloon. In one embodiment, the opto-electric device may include a light source constructed and arranged to emit at least one predetermined wavelength of light, and a light detector constructed and arranged to sense at least one predetermined wavelength of light and generate a signal in response thereto. In another embodiment, the light source and detector may consist of one or more optical fibers extending from the proximal end of the catheter to a location within the balloon enclosing the distal end of the catheter.

These and further objects, features, and advantages of the present invention will become apparent from the following detailed description, when reference is made to the figures in the accompanying drawings.

DETAILED DESCRIPTION OF THE INVENTION

The following detailed description should be read with reference to the drawings, in which like elements in different drawings are numbered in like fashion. The drawings, which are not necessarily to scale, depict selected embodiments and are not intended to limit the scope of the invention. Those skilled in the art will recognize that many of the examples provided may have suitable alternatives that could be utilized without departing from the spirit of the present invention.

Figure 1:
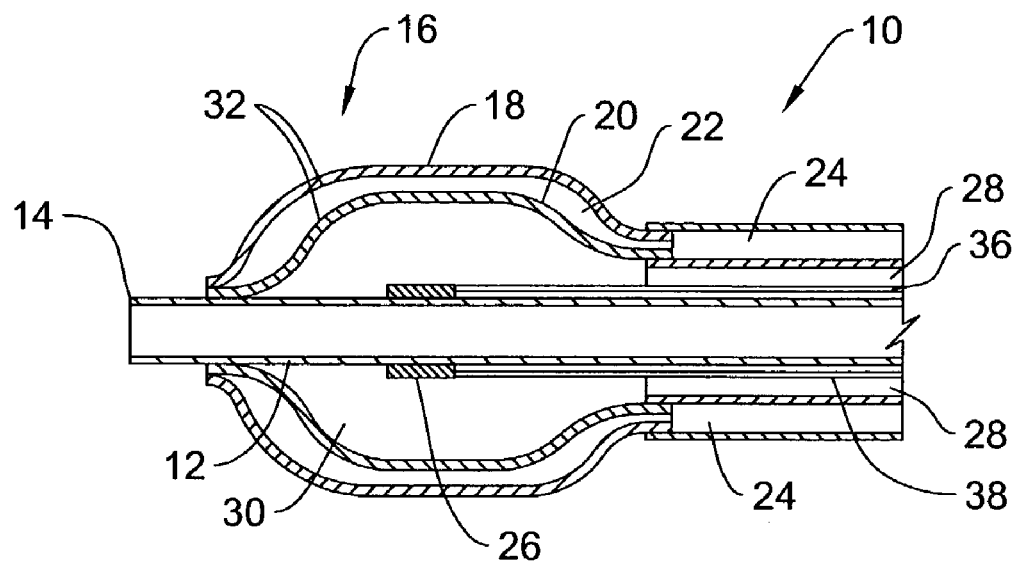
FIG. 1 shows one embodiment of a pH-measuring double-walled balloon disposed about the distal end of a catheter.

FIG. 1 illustrates one embodiment of a double-walled balloon system 10 that may be used for measuring the pH of the blood. System 10 may include an elongated shaft 12 having a proximal end (not shown) and a distal end 14, with a double-walled balloon 16 disposed about and proximate distal end 14 of elongated shaft 12. The double-walled balloon 16 may include a first material forming an outer wall 18 of the balloon and a second material forming an inner wall 20 of the balloon, such that the inner and outer walls, 20 and 18 respectively, enclose space 22 therebetween.

It is well known to those skilled in the art that a higher concentration of hydronium ions ($H_3O^+$) typically accompanies a lower pH. In view thereof, it may be advantageous in one embodiment for the outer wall 18 of the double-walled balloon 16 be made of a material permeable to hydronium ions ($H_3O^+$).

In the embodiments of the present invention, it is desirable for one or more property of the pH-sensitive compound to change as a function of the pH of the blood in the body vessel. Of the numerous pH-sensitive materials available, compounds that change their optical characteristics as a function of the pH of the blood may be more desirable than others. Some examples of such pH-sensitive material are: fluorescein, fluorescein derivatives, carboxynaphthofluorescein, seminaphthorhodafluors, and seminaphthofluoresceins. In view thereof, it may be advantageous for one or more of the walls of balloon 16 to be transparent to at least one predetermined wavelength of light.

In one embodiment, outer wall 18 of the double-walled balloon may be of a blood permeable material such that lipid-laden blood may flow into and out of enclosed space 22. The system of this embodiment may include a means for injecting and/or extracting pH-sensitive material in space 22 between the inner and outer walls, 20 and 18 respectively, of the double-walled balloon 16. The pH-sensitive material may be transported through a proximally extending lumen 24, fluidly coupled at its distal end to space 22. In an alternate embodiment, space 22 may be pre-filled with a pH-sensitive material such that lumen 24 may not be required. In other embodiments, the balloon walls 18 and/or 20 may be coated with a pH-sensitive material 32 such as polyacrylonitrile. Alternately, the balloon walls 18 and/or 20 may be made of a pH-sensitive material.

Measurement of the optical property and/or the change in the optical characteristics of a pH-sensitive compound may be accomplished using an opto-electric device 26 mounted on elongated shaft 12. As illustrated in FIG. 1, opto-electric device 26 may be located proximate distal end 14 of elongated shaft 12, and enclosed within double-walled balloon 16.

Opto-electric device 26 for measuring the optical characteristics of a pH-sensitive compound may include a light source and a light detector. The light source may be constructed and arranged to transmit at least one predetermined wavelength of light to the inner-most surface of the balloon. The light detector may be constructed and arranged to detect at least one predetermined wavelength of light, and generate a signal indicative of the wavelength of the detected light.

In one embodiment of the present invention, the light detector may detect light reflected and/or emanating from one or more surfaces of the one or more balloon walls. In an alternate embodiment, opto-electric device 26 may include a light directing means, constructed and arranged to direct at least one predetermined wavelength of light reflected from and/or emanating from at least one pH-sensitive material on the balloon 16. In another embodiment, the light detector may detect light reflected from the pH-sensitive material encased between the inner and outer walls, 20 and 18 respectively, of the double-walled balloon 16.

In one embodiment of the present invention, a light emitting diode may be used as the light source for opto-electric device 26. In an alternate embodiment, the light source may include at least one optical fiber 36 having a distal end and a proximal end (not shown), with the distal end positioned inside balloon 16 and the at least one optical fiber 36 extending from inside balloon 16 to the proximal end of elongated shaft 12. The at least one optical fiber 36 may be constructed and arranged to transmit at least one predetermined wavelength of light from the proximal end of the optical fiber to its distal end positioned inside balloon 16.

The light detector in one embodiment of the invention may include at least one optical fiber 38 having a distal end and a proximal end (not shown), with the distal end positioned inside balloon 16 and the at least one optical fiber 38 extending from inside balloon 16 to the proximal end of elongated shaft 12. The at least one optical fiber 38 may be constructed and arranged to transmit at least one predetermined wavelength of light from its distal end positioned inside balloon 16 to the proximal end of the optical fiber 38.

Opto-electric device 26 may further include a light directing device constructed and arranged to direct at least one predetermined wavelength of light, at least in part, onto at least one pH-sensitive material. The light directing device may be positioned inside balloon 16, and may be constructed and arranged to enable movement along the longitudinal axis inside balloon 16, and rotation about the longitudinal axis inside balloon 16. As such, the light directing device may be used to direct at least one predetermined wavelength of light to and/or from any location inside balloon 16.

In alternate embodiments of the present inventions, opto-electric device 26 may include an optical filter for filtering at least a portion of at least one predetermined wavelength of light to and/or from the light source and/or the light detector. Opto-electric device 26 may also include one or more optical lenses for collimating at least one predetermined wavelength of light to and/or from the light source and/or the light detector.

After positioning balloon 16 in the vicinity of a vulnerable plaque, it may be advantageous to inflate balloon 16 to somewhat occlude blood flow, thereby enabling lipid laden blood to flow through outer wall 18 and into enclosed space 22 wherein the blood can come into contact with a pH-sensitive material. Another advantage of inflating balloon 16 may be to permit a larger surface area of balloon outer wall 18 to be exposed to the blood in the body vessel. This may be desirable for systems having a pH-sensitive material coated on the surface of the balloon walls, and for systems in which the balloon walls are made of a pH-sensitive material. Balloon 16 may be inflated and/or deflated via a proximally extending lumen 28, fluidly coupled at its distal end to space 30 inside balloon 16, and fluidly coupled at its proximal end to an inflation/deflation means.

Figure 2:
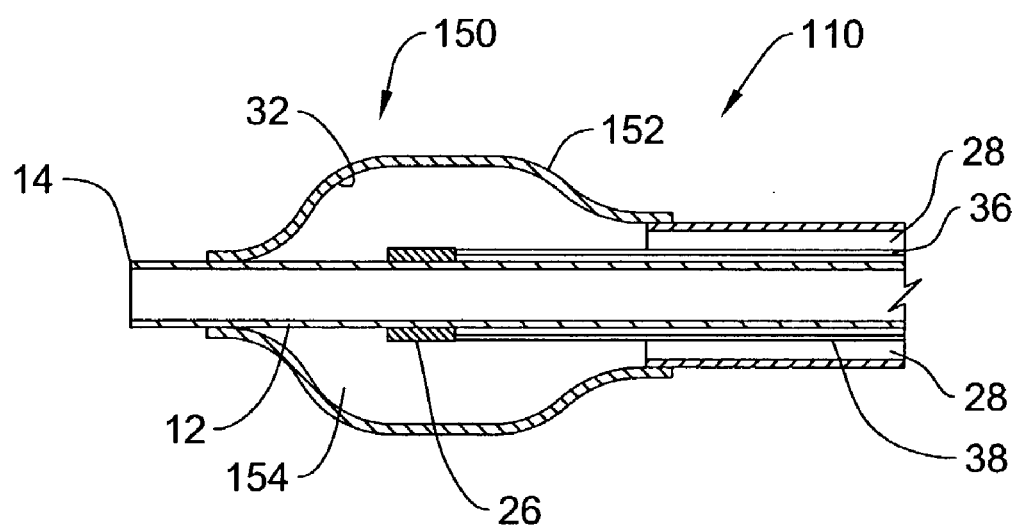
FIG. 2 shows one embodiment of a pH-measuring single-walled balloon disposed about the distal end of a catheter.

FIG. 2 illustrates one embodiment of a single-walled balloon system 110 that may be used for measuring the pH of blood within the vasculature. System 110 may include an elongated shaft 12 having a proximal end (not shown) and a distal end 14, with a single-walled balloon 150 disposed about and proximate distal end 14 of elongated shaft 12. Single-walled balloon 150 may include wall 152 defining the outermost extent of balloon 150 and enclosing space 154.

Balloon wall 152, in many respects, may be similar to outer wall 18 of doublewall balloon 16 discussed above with respect to FIG. 1. Balloon wall 152 may be permeable to lipid laden blood, may be coated with a pH-sensitive compound 32, or may be of a pH-sensitive material. Balloon 150 may be inflated by injecting a pH-sensitive fluid through proximally extending lumen 28. As previously discussed in the various embodiments related to FIG. 1, it may be desirable to use a pH-sensitive material whose optical property changes in response to the pH of the blood in the vasculature. Similarly, measurement of the optical property and/or the change in the optical characteristics of the pH-sensitive compound may be accomplished using opto-electric device 26 mounted on elongated shaft 12 proximate distal end 14 and enclosed in balloon 150.

In use, either system 10 (FIG. 1) of the present invention having a double-walled balloon 16, or system 110 (FIG. 2) of the present invention having a single-walled balloon 150 may be introduced into the vasculature, and balloon 16 or 150 positioned in the vicinity of a vulnerable plaque. In some instances, it may be desirable to position the balloon at a location immediately distal of the lesion to enhance contact between lipid laden blood and the balloon. The balloon may then be inflated to enable blood to enter space 22 or 154 wherein it contacts the pH-sensitive fluid contained therein. Alternately, the blood within the body vessel may interact with the one or more pH-sensitive walls of the inflated balloon. When lipid laden blood having a lower pH comes in contact with the pH-sensitive material, it may change the optical characteristics of the pH-sensitive material. Measurement of the optical property and/or the change in the optical characteristics of the pH-sensitive compound may be accomplished using the opto-electric device 26 mounted on elongated shaft 12. Upon completion of the procedure, the balloon may be deflated, and then removed from the vasculature.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

We claim:

1. A device for detecting plaque within a body vessel, said device comprising:
   an elongated shaft having a proximal end and a distal end;
   a double-walled balloon disposed about a portion of the elongated shaft proximate the distal end of the elongated shaft; and
   means for detecting the pH of the material in the body vessel.

2. The device of claim 1, wherein the double-walled balloon comprises a first material forming an outer wall of the balloon and a second material forming an inner wall of the balloon, said inner and outer walls enclosing a space therebetween.

3. The device of claim 2, wherein the first material forming the outer wall of the double-walled balloon is permeable to one or more pH-indicative compounds.

4. The device of claim 3, wherein the space enclosed between the inner and outer walls of the double-walled balloon contains a pH-sensitive material.

5. The device of claim 4, wherein one or more properties of the pH-sensitive material changes as a function of the pH of the one or more pH-indicative compounds crossing the outer wall of the double-walled balloon.

6. The device of claim 4, wherein the pH-sensitive material has optical characteristics that change as a function of the pH of the one or more pH-indicative compounds crossing the outer wall of the double-walled balloon.

7. The device of claim 4, wherein the pH-sensitive material is selected from the group consisting of seminaphthofluoresceins, fluorescein, carboxynaphthofluorescein, seminaphthorhodafluors, and fluorescein derivatives.

8. The device of claim 2, wherein the elongated shaft further comprises means for injecting and/or extracting pH-sensitive material in the space between the inner and outer walls of the double-walled balloon.

9. The device of claim 2, wherein the first material forming the outer wall of the double-walled balloon is permeable to hydronium ions ($H_3O^+$).

10. The device of claim 1, wherein the balloon has an inflated state and a deflated state.

11. The device of claim 1, wherein the elongated shaft further comprises a means for inflating and/or deflating the balloon.

12. The device of claim 1, wherein the walls of the balloon are transparent to at least one predetermined wavelength of light.

13. The device of claim 1, wherein the means for detecting the pH is an opto-electric device.

14. The device of claim 13, wherein the opto-electric device detects a change of the pH of the material in the body vessel.

15. The device of claim 13, wherein the opto-electric device detects a change in one or more optical characteristics of pH-sensitive material coated on the outer surface of the balloon.

16. The device of claim 13, wherein the opto-electric device detects a change in one or more optical characteristics of the pH-sensitive material between the inner and outer walls of the double-walled balloon.

17. The device of claim 13, wherein the opto-electric device detects a change in one or more optical characteristics of pH-sensitive material comprising one or more walls of the balloon.

18. The device of claim 13, wherein the opto-electric device comprises:
   a light source constructed and arranged to transmit at least one predetermined wavelength of light to the innermost surface of the balloon; and
   a light detector constructed and arranged to detect at least one predetermined wavelength of light and generate a signal indicative of the wavelength of light.

19. The device of claim 18, wherein the light detector detects light reflected from one or more surfaces of the balloon walls.

20. The device of claim 19, further comprising a light directing device, said light directing device constructed and arranged to direct at least one predetermined wavelength of light reflected from and/or emanating from at least one pH-sensitive material comprising the balloon.

21. The device of claim 18, wherein the light detector detects light reflected from the pH-sensitive material between the inner and outer walls of the double-walled balloon.

22. The device of claim 18, wherein the light detector detects light emanating from the balloon walls.

23. The device of claim 18, wherein the light detector detects light emanating from the pH-sensitive material between the inner and outer walls of the double-walled balloon.

24. The device of claim 18, wherein the light detector is positioned inside the balloon.

25. The device of claim 18, wherein the light source is positioned inside the balloon.

26. The device of claim 18, wherein the light source is a light emitting diode.

27. The device of claim 18, wherein the light source comprises at least one optical fiber having a distal end and a proximal end, said distal end of the optical fiber positioned inside the balloon and said optical fiber extending from inside the balloon to the proximal end of the elongated shaft, the optical fiber constructed and arranged to transmit at least one predetermined wavelength of light from the proximal end of said optical fiber to the inside of the balloon.

28. The device of claim 18, wherein the light detector comprises at least one optical fiber having a distal end and a proximal end, said distal end of the optical fiber positioned inside the balloon and said optical fiber extending from inside the balloon to the proximal end of the elongated shaft, the optical fiber constructed and arranged to transmit at least one predetermined wavelength of light from the inside of the balloon to the proximal end of said optical fiber.

29. The device of claim 18, further comprising a light directing device constructed and arranged to direct at least one predetermined wavelength of light onto at least one pH-sensitive material comprising the balloon.

30. The device of claim 29, wherein the light directing device is positioned inside the balloon.

31. The device of claim 29, wherein the light directing device is constructed and arranged to move along a longitudinal axis inside the balloon.

32. The device of claim 29, wherein the light directing device is constructed and arranged to rotate about a longitudinal axis inside the balloon.

33. The device of claim 29, wherein the light directing device is constructed and arranged to direct at least one predetermined wavelength of light to and/or from any location inside the balloon.

34. The device of claim 29, further comprising an optical filter constructed and arranged to filter at least a portion of at least one predetermined wavelength of light to and/or from the light source.

35. The device of claim 29, further comprising an optical filter constructed and arranged to filter at least a portion of at least one predetermined wavelength of light to and/or from the light detector.

36. The device of claim 29, further comprising at least one optical lens constructed and arranged to collimate at least one predetermined wavelength of light to and/or from the light source.

37. The device of claim 29, further comprising at least one optical lens constructed and arranged to collimate at least one predetermined wavelength of light to and/or from the light detector.

38. A device for detecting plaque within a body vessel, said device comprising:
   an elongated shaft having a proximal end and a distal end;
   a balloon disposed about a portion of the elongated shaft proximate the distal end of the elongated shaft; wherein the outer surface of the ballon further comprises a pH-sensitive material; and
   means for detecting the pH of the material in the body vessel.

39. The device of claim 38, wherein the pH-sensitive material changes one or more property of the balloon as a function of the pH of the material in the body vessel.

40. The device of claim 38, wherein one or more properties of the pH-sensitive material change as a function of the pH of the material in the body vessel.

41. The device of claim 38, wherein the pH-sensitive material is polyacrylonitrile.

42. The device of claim 38, wherein the balloon is constructed from a pH-sensitive material.

43. The device of claim 38, wherein the balloon has an inflated state and a deflated state.

44. The device of claim 38, wherein the means for detecting the pH is an opto-electric device.

45. The device of claim 38, wherein the balloon is transparent to at least one predetermined wavelength of light.

46. A method for detecting plaque within a body vessel, said method comprising the steps of:
   providing a catheter comprising an elongated shaft having a proximal end and a distal end, an inflatable double-walled balloon having an inner wall and an outer wall permeable to pH-indicative compound, said inner and outer walls enclosing a space for holding a pH-sensitive material therebetween, said double-walled balloon disposed about a portion of the elongated shaft proximate the distal end of said elongated shaft;
   inserting the distal end of the catheter into a body vessel, positioning the double-walled balloon proximate a plaque, inflating said double-walled balloon enabling contact between the outer-most surface of the double-walled balloon and one or more pH-indicative compounds to enable flow of said pH-indicative compound across said permeable outer wall of the double-walled balloon; and
   measuring the pH of the material within the body vessel by detecting a change in one or more properties of the pH-sensitive material enclosed between the inner and outer walls of the double-walled balloon.

47. The method of claim 46, further comprising the step of injecting and/or extracting a pH-sensitive material between the inner and outer walls of the double-walled balloon.

48. A method for detecting plaque within a body vessel, said method comprising the steps of:
   providing a catheter comprising an elongated shaft having a proximal end and a distal end, an inflatable single-walled balloon having a pH-sensitive material on the outer surface of the balloon wall, said single-walled balloon disposed about a portion of the elongated shaft proximate the distal end of said elongated shaft;
   inserting the distal end of the catheter into a body vessel, positioning the single-walled balloon proximate a plaque, inflating said single-walled balloon enabling contact between the outer-most surface of the single-walled balloon and one or more pH-indicative compounds in the body vessel; and
   measuring the pH of the material within the body vessel by detecting a change in one or more property of the pH-sensitive material on the outer surface of the single-walled balloon.

49. A method for detecting plaque within a body vessel, said method comprising the steps of:
   providing a catheter comprising an elongated shaft having a proximal end and a distal end, an inflatable balloon comprised of a pH-sensitive material, said balloon disposed about a portion of the elongated shaft proximate the distal end of said elongated shaft;
   inserting the distal end of the catheter into a body vessel, positioning said balloon proximate a plaque, inflating the balloon enabling contact between the outer-most surface of the balloon and one or more pH-indicative compounds in the body vessel; and
   measuring the pH of the material within the body vessel by detecting a change in one or more properties of the wall comprising the inflatable balloon.

* * * * *

UNITED STATES PATENT AND TRADEMARK OFFICE
CERTIFICATE OF CORRECTION

| | | |
|---|---|---|
| PATENT NO. | : 6,999,807 B2 | Page 1 of 1 |
| APPLICATION NO. | : 10/349674 | |
| DATED | : February 14, 2006 | |
| INVENTOR(S) | : Scott R. Smith et al. | |

It is certified that error appears in the above-identified patent and that said Letters Patent is hereby corrected as shown below:

On Title page, Item (54) col. 1, please delete "PH" and insert --pH--therefor;

On Title page, Abstract, Item (57) col. 2, line 12, please delete "PII" and insert --pH-- therefor;

Title Page (Page 2), Item (56), References Cited, please add --

DE                    3 523 987                  01-1987--;

Column 6, line 33 (Claim 21), please delete "the";
Column 6, line 39 (Claim 23), please delete "the".

Signed and Sealed this

Twenty-second Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,999,807 B2
APPLICATION NO. : 10/349674
DATED : February 14, 2006
INVENTOR(S) : Scott R. Smith et al.

Page 1 of 1

It is certified that error appears in the above-identified patent and that said Letters Patent is hereby corrected as shown below:

Item (54) col. 1
Title Page, Title of Invention, please delete "PH" and insert --pH--therefor;
Item (57) col. 2
Title Page, Abstract, last line, please delete "PII" and insert --pH--therefor;
Item (56)
Title Page (Page 2), References Cited, please add --

DE                      3 523 987                      01-1987--;

Column 6, line 33 (Claim 21), please delete "the";

Column 6, line 39 (Claim 23), please delete "the";

Signed and Sealed this

Fifth day of September, 2006

JON W. DUDAS
*Director of the United States Patent and Trademark Office*